United States Patent
Han et al.

(10) Patent No.: US 6,821,651 B2
(45) Date of Patent: Nov. 23, 2004

(54) RED FLUORESCENT MATERIAL AND ORGANIC ELECTROLUMINESCENT DEVICE CONTAINING SAME

(75) Inventors: Ki-Jong Han, Cheongju-si (KR); Ha-Keun Hwang, Seongnam-si (KR); Dae-Seok Jun, Seoul (KR); Ji-Hwan Keum, Pusan (KR); Young-Kyoo Kim, Pusan (KR)

(73) Assignee: Nessdisplay Co., Ltd. (KR)

( * ) Notice: Subject to any disclaimer, the term of this patent is extended or adjusted under 35 U.S.C. 154(b) by 0 days.

(21) Appl. No.: 10/432,065

(22) PCT Filed: Nov. 29, 2001

(86) PCT No.: PCT/KR01/02062

§ 371 (c)(1),
(2), (4) Date: May 19, 2003

(87) PCT Pub. No.: WO02/44302

PCT Pub. Date: Jun. 6, 2002

(65) Prior Publication Data

US 2004/0014392 A1 Jan. 22, 2004

(30) Foreign Application Priority Data

Nov. 29, 2000 (KR) ........................ 2000-71665

(51) Int. Cl.$^7$ ........................ H05B 33/14; C09K 11/06; B32B 9/00; C07D 407/14; C07D 491/06
(52) U.S. Cl. .................. 428/690; 428/917; 252/301.16; 313/504; 313/506; 445/52
(58) Field of Search ................................ 428/690, 917, 428/500; 252/301.16; 313/504, 506; 445/52

(56) References Cited

U.S. PATENT DOCUMENTS

| 4,948,893 | A | * | 8/1990 | Chen et al. ................... 546/66 |
| 5,518,825 | A | * | 5/1996 | Murayama et al. ......... 428/690 |
| 5,935,720 | A | * | 8/1999 | Chen et al. ................. 428/690 |
| 6,455,579 | B1 | * | 9/2002 | Satsuki et al. .............. 514/457 |

OTHER PUBLICATIONS

Chen et al., Thin Solid Films, vol. 363, (2000), pp. 327–331.*

* cited by examiner

Primary Examiner—Dawn Garrett
(74) Attorney, Agent, or Firm—Anderson Kill & Olick, PC

(57) ABSTRACT

A novel red fluorescent material of formula (I) of the present invention has an improved thermostability, and an organic electroluminescent device containing the fluorescent material of formula (I) can provide color ranging from orange to deep red.

6 Claims, 7 Drawing Sheets

RED FLUORESCENT MATERIAL AND ORGANIC ELECTROLUMINESCENT DEVICE CONTAINING SAME

FIELD OF THE INVENTION

The present invention relates to a novel compound having red-color luminescent characteristics, a process for the preparation thereof and an organic electroluminescent device containing same.

BACKGROUND OF THE INVENTION

Conventional red fluorescent materials used in organic electroluminescent devices generally belong to a class of compounds having an alkyl substituted nitrogen group, e.g., —N(CH$_3$)$_2$, as in 4-(dicyanomethylene)-2-methyl-6-(4-dimethylaminostyryl)4H-pyran (DCM).

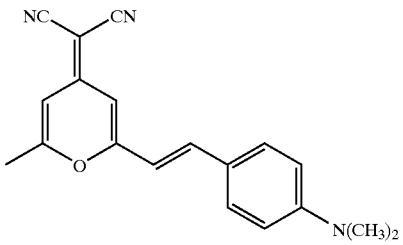

However, such compounds exhibit low heat stability due to the presence of alkyl substituents, and give partial orange luminescent characteristics, failing to exhibit deep red.

SUMMARY OF THE INVENTION

Accordingly, it is a primary object of the present invention to provide a novel red fluorescent compound having improved thermostability and being capable of emitting color in the range of orange to deep red.

It is another object of the present-invention to provide a process for preparing said compound.

It is a further object of the present invention to provide an organic electroluminescent device comprising said compound.

In accordance with one aspect of the present invention, there is provided a novel red fluorescent compound of formula (I):

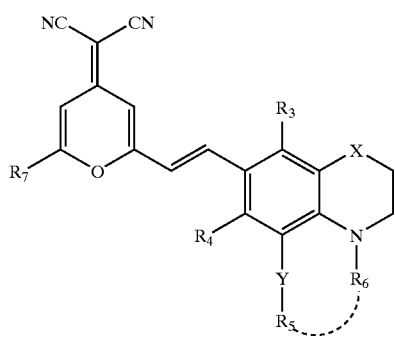

(I)

wherein,

X is CR$_1$R$_2$, NR', oxygen or sulfur;
Y is NH, oxygen or sulfur;

R', R$_1$, R$_2$, R$_3$, R$_4$, R$_5$, R$_6$ and R$_7$ are each independently hydrogen, C$_{1-4}$ alkyl, C$_{1-4}$ alkoxy, aryl, or aryl substituted with C$_{1-4}$ alkyl or C$_{1-4}$ alkoxy, R$_5$ and R$_6$ being optionally fused to form a hetero-ring.

BRIEF DESCRIPTION OF THE DRAWINGS

The above and other objects and features of the present invention will become apparent from the following description, when taken in conjunction with the accompanying drawings, which respectively show.

DETAILED DESCRIPTION OF THE INVENTION

Figure 1:
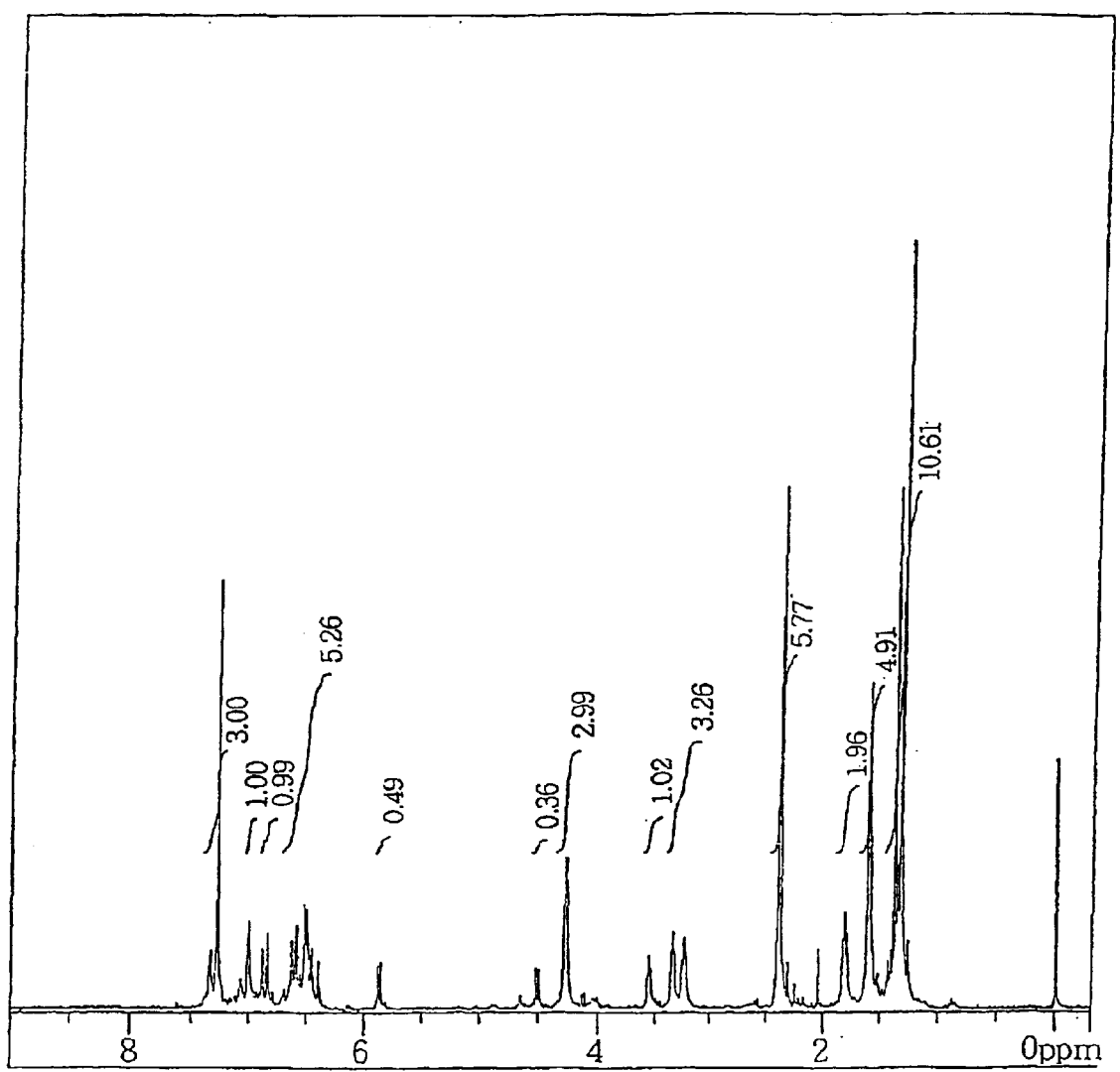
FIGS. 1 to 3: NMR spectra of the novel red fluorescent compounds prepared in Examples 1 to 3, respectively.

Preferred among the compounds of formula (I) of the present invention are those obtained when X is CR$_1$R$_2$ or oxygen, Y is oxygen or sulfur, and R' and R$_1$ to R$_7$ are each independently hydrogen, methyl, isopropyl, t-butyl, methoxy, phenyl, phenyl substituted with methyl, or benzyl; and more preferred are those obtained when X is CR$_1$R$_2$, Y is oxygen, and R' and R$_1$ to R$_7$ are each The process for preparing the compound of formula (I) of the present invention may be conducted in accordance with Reaction Scheme A as described below:

Reaction Scheme A

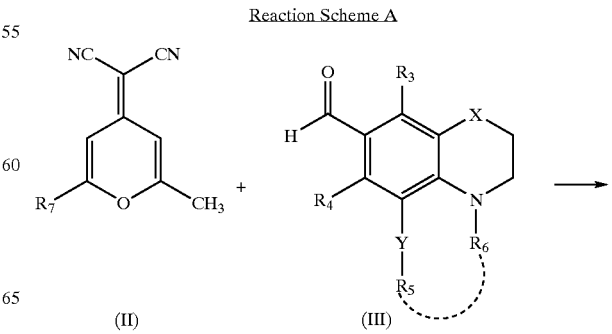

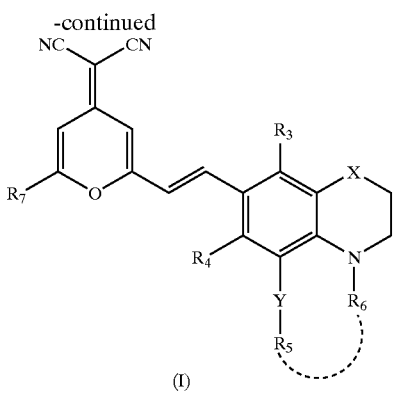

(I)

wherein, X, Y, R', and R₁ to R₇ have the same meanings as defined above.

Specifically, a compound of formula (I) may be prepared by reacting a pyran derivative of formula (II) with an aldehyde derivative of formula (III) in an alcohol solvent, e.g., methanol, ethanol and propanol, in the presence of an amine such as piperidine. Alternatively, it may be prepared by reacting a compound of formula (II) with a compound of formula (III) in a solvent such as acetic anhydride in the presence of an acid such as phosphoric acid. Such reactions may be performed using molar equivalent amounts of the reactants at a temperature ranging from room temperature to the boiling point of the solvent.

A compound of formula (II) employed in the inventive reaction is commercially available, or it may be synthesized in accordance with the method disclosed in U.S. Pat. No. 5,908,581.

In addition, a compound of formula (III) may be prepared, in accordance with the Vilsmeier method, by reacting a hetero-ring compound of formula (IV) with $POCl_3$ in an organic solvent such as dimethylformamide (DMF) as shown in Scheme Reaction B (see U.S. Pat. No. 2,558,285):

Reaction Scheme B

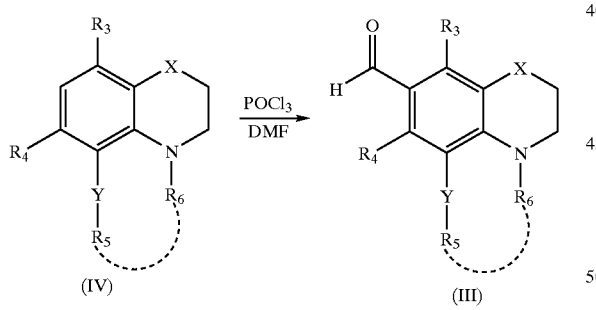

wherein, X, Y, R', and R₁ to R₆ have the same meanings as defined above.

The organic electroluminescent device of the present invention comprises an organic luminescent layer containing compound of formula (I). The inventive electroluminescent device may be prepared by sequentially stacking on an ITO-coated glass substrate, a hole transport layer, said organic luminescent layer, an electron transport layer (or a luminescent/electron transport layer) and a metallic electrode layer, in accordance with a conventional method.

Preferably, the inventive compound of formula (I) may be employed as a doping material for red or orange luminescence.

The hole transport layer, luminescent layer and electron transport layer of the inventive electroluminescent device may be formed by a conventional method which may be a wet process, e.g., a spin-coating, doctor-blading, roll-printing and screen-printing method, or a chemical vapor deposition process. The metallic cathode layer may be formed by vapor deposition.

Active materials used in the hole transport and electron transport layers may be selected from any of those known in the art, and for the cathode layer, for instance, aluminum, silver, calcium, magnesium, copper or an alloy thereof may be used.

The novel red fluorescent material of the present invention has improved thermostability, and the organic electroluminescent device containing same is capable of emitting color in the range of orange to deep red.

The present invention is further described and illustrated in Example, which is, however, not intended to limit the scope of the present invention.

PREPARATION EXAMPLE 1

Preparation of 6,6-dimethyl-3,4,5,6-tetrahydro-2H-1-oxa-3a-aza-phenalene-8-carbaldehyde (Compound of Formula (III-a))

The title compound, one of the starting materials for the preparation of the compound of formula (I), was prepared in accordance with Reaction Scheme C as described below:

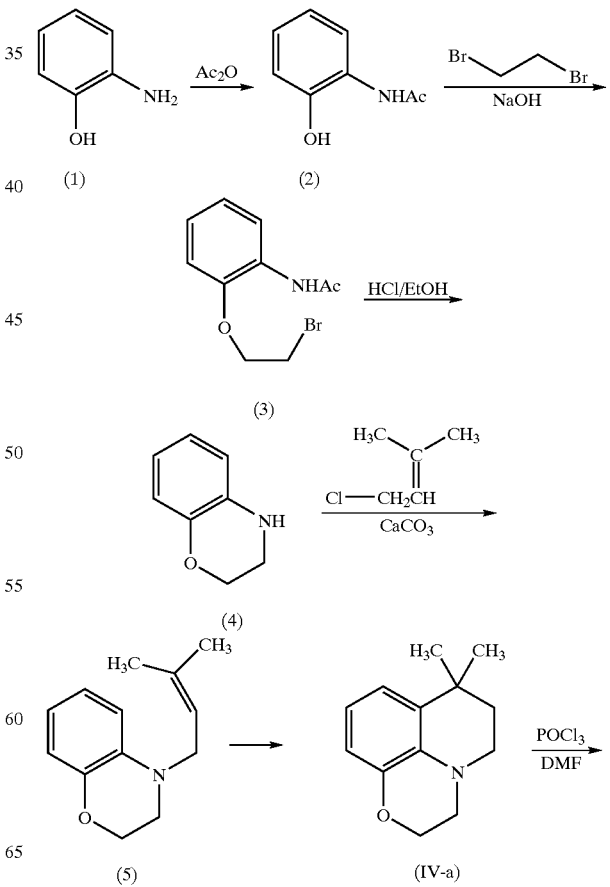

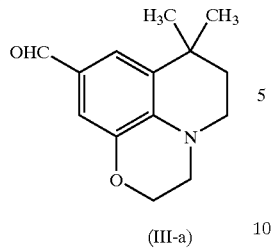

(III-a)

Specifically, 10.91 g (0.1 mol) of o-aminophenol (compound (1)) was dissolved into 120 ml of isopropanol and cooled to 0° C., and 12.4 g (0.12 mol) of acetic anhydride was added thereto and kept at 0~25° C. for 1 hour with stirring. Then, the solvent was removed from the reaction mixture under a reduced pressure to obtain 14.6 g (yield: 98%) of compound (2). Compound (2), 34 ml (4.0 molar equivalent) of dibromoethane and 4.58 g of NaOH (1.1 molar equivalent) were added to 150 ml of isopropanol and kept at 55~65° C. for 2 hours to carry out alkylation. The resulting solution was filtered at 50° C. to remove insoluble materials and the solvent was distilled off to obtain 10.3 g (yield: 40%) of compound (3).

Compound (3) was dissolved in a mixture of 120 ml of 6N HCl and 120 ml of ethanol, and heated for 12 hours, followed by distillation of ethanol. The resulting solution was neutralized with NaOH, extracted with ethyl acetate, and the solvent was distilled off to obtain 4.921 g (yield: 91%) of compound (4). Compound (4), 4.183 g of 4-chloro-2-methyl-2-butene and 2 g of calcium carbonate were added to 30 ml of DNW, and kept at 70° C. for 3 hours to carry out N-alkylation. After adding 90 ml of water, the resulting solution was extracted with ethyl acetate and the solvent was distilled off to obtain 6.4 g (yield: 86.5%) of compound (5). Compound (5) was added to 20 ml of methanesulfonic acid and kept at 100° C. for 2 hours to obtain 3.4 g (yield: 54%) of compound (IV-a).

In order to introduce an aldehyde group to compound (IV-a), 1.83 ml of POCl$_3$ was added to 10 ml of DMF, cooled to 0° C., and a solution of compound (IV-a) in 5 ml of DMF was added thereto. The mixture was heated to 45° C. and then kept for 12 hours. The reaction mixture was poured into a mixture of 10 g of ice and 40 g of water, neutralized with NaOH and extracted with chloroform, followed by purification by silica gel chromatography using a mixture of ethyl acetate and hexane (1/4), to obtain 2.527 g (yield: 65.4%) of the title compound.

$^1$H NMR (CDCl$_3$, 200MHz) δ (ppm) 1.28(s, 6H), 1.77(t, 2H), 3.25(t, 2H), 3.35(t, 2H), 4.21(t, 2H), 7.08(s, 1H), 7.34(s, 1H), 9.62(s, 1H)

PREPARATION EXAMPLE 2

Preparation of 8-methoxy-1,4,4-trimethyl-1,2,3,4-tetra-hydro-quinoline-6-carbaldehyde (Compound of Formula (III-b))

The title compound, another starting material for the preparation of the compound of formula (I), was prepared in accordance with Reaction Scheme D as described below:

Reaction Scheme D

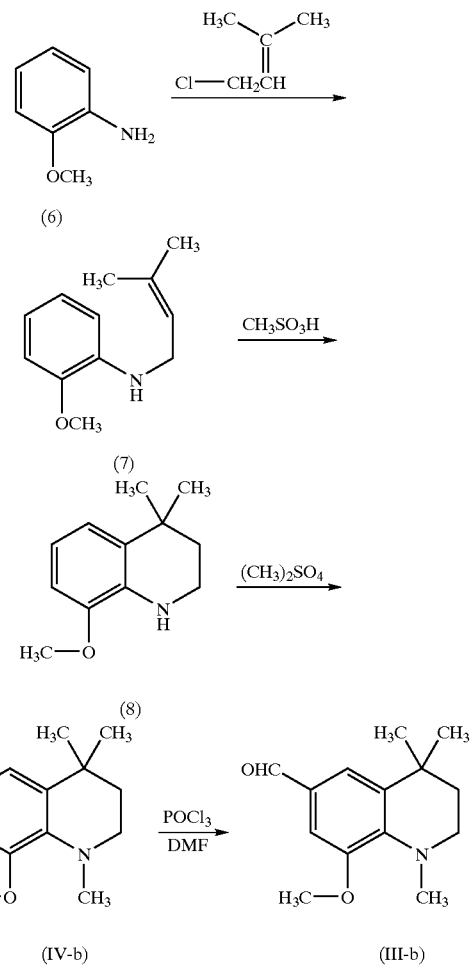

Specifically, 12.32 g (0.1 mol) of o-anicidine (compound (6)), 6 g of calcium carbonate and 10.458 g of 4-chloro-2-methyl-2-butene were added to 20 ml of DMF and kept at 50° C. for 3 hours with stirring to effect N-alkylation. After adding 90 ml of water, the reaction mixture was extracted with ethyl acetate and the solvent was distilled off to obtain 18.47 g (yield: 95.1%) of compound (7). Compound (7) was added to 55 ml of methanesulfonic acid and kept at 100° C. for 2 hours with stirring to obtain 9.5 g (yield: 55.1%) of compound (8).

2.521 g (13.18 mmol) of compound (8) was dissolved in 10 ml of DMF, 2.71 g of dimethylsulfate was added thereto, and kept at 65~70° C. for 2 hours with stirring, to obtain 1.12 g (yield: 41.4%) of compound (IV-b). In order to introduce an aldehyde group to compound (IV-b), 0.61 ml of POCl$_3$ was added to was added thereto. The mixture was heated to 45° C. and then kept for 12 hours. The reaction mixture was poured into a mixture of 5 g of ice and 20 g of water, neutralized with NaOH, and extracted with chloroform, followed by purification by silica gel chromatography using a mixture of ethyl acetate and hexane (1/4), to obtain 0.959 g (yield: 75.1%) of the title compound.

$^1$H NMR (CDCl$_3$, 200MHz) δ (ppm) 1.29(s, 6H), 1.70(t, 2H), 2.85(s, 3H), 3.14(t, 2H), 3.85(s, 3H), 7.08(s, 1H), 7.37(s, 1H), 9.67(s, 1H)

PREPARATION EXAMPLE 3

Preparation of 5,8-dimethoxy-1,4,4-trimethyl-1,2,3,4-tetrahydro-quinoline-6-carbaldehyde (Compound of Formula (III-c))

The title compound was prepared in accordance with Reaction Scheme E as described below:

Reaction Scheme E

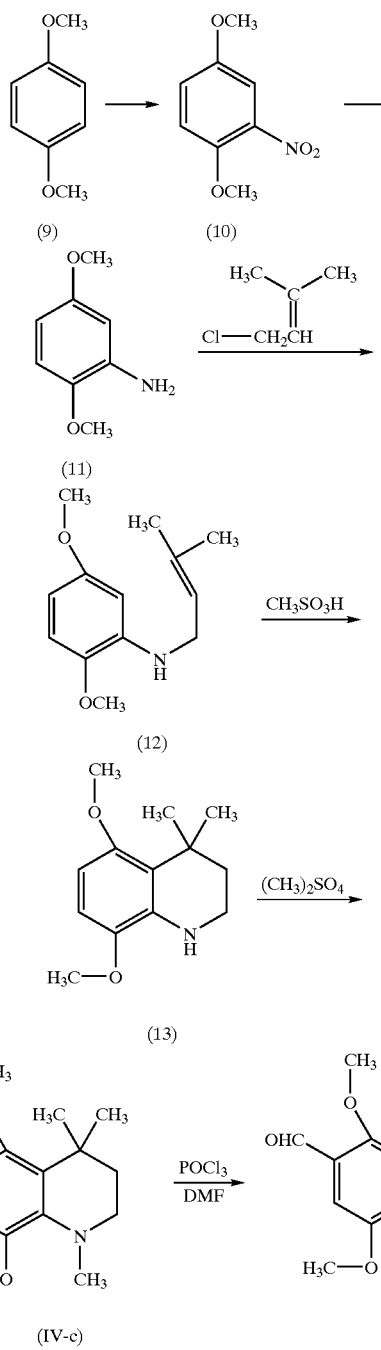

Specifically, 13.815 g (0.1 mol) of dimethoxybenzene (compound (9)) was added to 150 ml of acetic acid, heated at 50° C., and then 10.52 g of 60% nitric acid was added thereto. The solution became light yellow and its temperature rose to 60~70° C. The reaction mixture was allowed to cool and poured into 1 L of water, when precipitates formed. Compound (10) separated by filtration was suspended into 300 ml of ethanol. 1 ml of conc. HCl and 18.43 g of Fe were added to the suspension in sequence, heated for 3 hours to carry out reduction, to obtain 8.88 g (yield: 58%) of compound (11).

Compound (11), 3.2 g of calcium carbonate and 6.07 g of 4-chloro-2-methyl-2-butene were added to 80 ml of DMF and kept at 50° C. for 3 hours with stirring to perform N-alkylation. 200 ml of water was added to the reaction mixture, extracted with ethyl acetate, and the solvent was distilled off to obtain 6.78 g (yield: 52.81%) of compound (12). Compound (12) was added to 50 ml of methanesulfonic acid, and kept at 100° C. for 2 hours with stirring to obtain 3.91 g (yield: 57.71%) of compound (13).

2.9 g (13 mmol) of compound (13) was dissolved into 16 ml of DMF, 1.82 g of dimethylsulfate was added thereto, and kept at 65~70° C. for 2 hours with stirring to obtain 1.65 g (yield: 53.4%) of compound (IV-c). In order to introduce an aldehyde group to compound (IV-c), 0.77 ml of $POCl_3$ was added to 10 ml of DMF, cooled to 0° C. and a solution of compound (IV-c) in 4ml of DMF was added thereto. The mixture was heated to 45° C. and then kept for 12 hours. The reaction mixture was poured into a mixture of 10 g of ice and 30 g of water, neutralized with NaOH, and extracted with chloroform, followed by purification by silica gel chromatography using a mixture of ethyl acetate and hexane (1/4), to obtain 1.324 g (yield: 71.8%) of the title compound.

$^1$H NMR ($CDCl_3$, 200 MHz) δ (ppm) 1.29(s, 6H), 1.69(t, 2H), 2.95(s, 3H), 3.13(t, 2H), 3.81(s, 3H), 3.92(s, 3H), 7.30(s, 1H), 9.65(s, 1H)

PREPARATION EXAMPLE 4

Preparation of 1-benzyl-8-methoxy-4,4-dimethyl-1,2,3,4-tetrahydro-quinoline-6-carbaldehyde (Compound of Formula (III-b))

The title compound was prepared in accordance with Reaction Scheme F as described below:

Reaction Scheme F

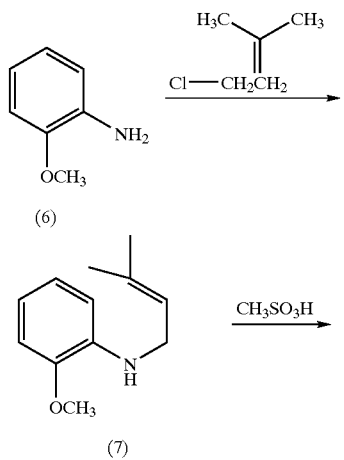

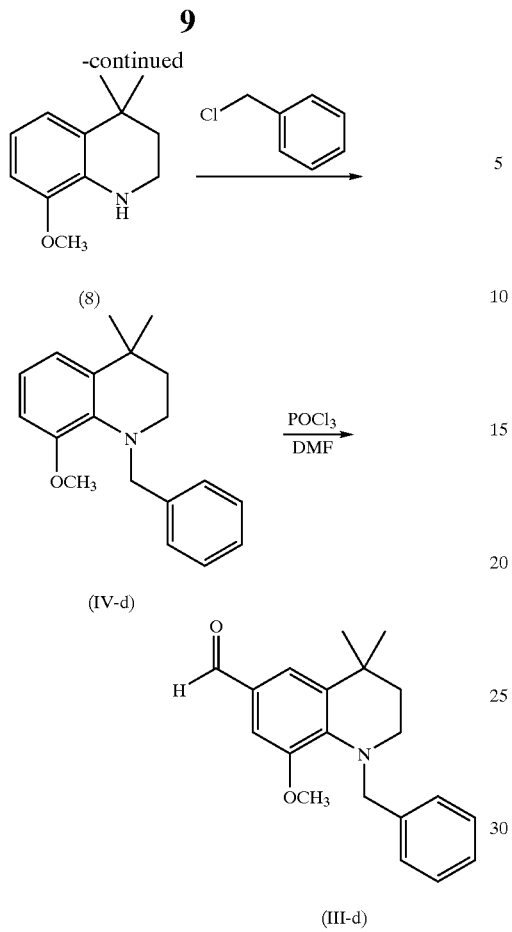

(8)

(IV-d)

(III-d)

Specifically, 12.32 g (0.1 mol) of o-anicidine (compound (6)), 6 g of calcium carbonate and 10.458 g of 4-chloro-2-methyl-2-butene were added to 20 ml of DMF and kept at 50° C. for 3 hours with stirring to perform N-alkylation. 90 ml of water was added to the reaction mixture, extracted with ethyl acetate, and the solvent was distilled off to obtain 18.47 g (yield: 95.1%) of compound (7). Compound (7) was added to 55nm of methanesulfonic acid and kept at 100° C. for 2 hours with stirring to obtain 9.5 g (yield: 55.1%) of compound (8).

2.521 g (13.18 mmol) of compound (8) was dissolved in 10 ml of DMF, 1.668 g (13.18 mmol) of benzyl chloride was added thereto, and kept at 65~70° C. for 2 hours with stirring, to obtain 3.1 g (yield: 83.7%) of compound (IV-d). In order to introduce an aldehyde group to compound (IV-d), 2.53 g of POCl$_3$ was added to. 10 ml of DMF cooled to 0° C. and a solution of compound (IV-d) in 2 ml of DMF was added thereto. The mixture was heated to 45° C. and then kept for 12 hours. The reaction mixture was poured into a mixture of 5 g of ice and 20 g of water, neutralized with NaOH, and extracted with chloroform, followed by purification by silica gel chromatography using a mixture of ethyl acetate and hexane (1/4), to obtain 2.3 g (yield: 67.4%) of the title compound.

$^1$H NMR (CDCl$_3$, 200 MHz) δ (ppm) 1.29(s, 6H), 1.67(t, 2H), 3.08(t, 2H), 3.87(s, 3H), 4.41(s, 2H), 7.10-7.40(m, 7H), 9.70(s, 1H)

EXAMPLE 1

Preparation of 2-{2-[2-(6,6-dimethyl-3,4,5,6-tetrahydro-2H-1-oxa-3a-aza-phenalen-8-yl)-vinyl]-6-methyl-pyran-4-ylidene}-malonitrile (Compound of Formula (I-a))

The compound of formula (I) of the present invention was prepared in accordance with Reaction Scheme G as described below:

Reaction Scheme G

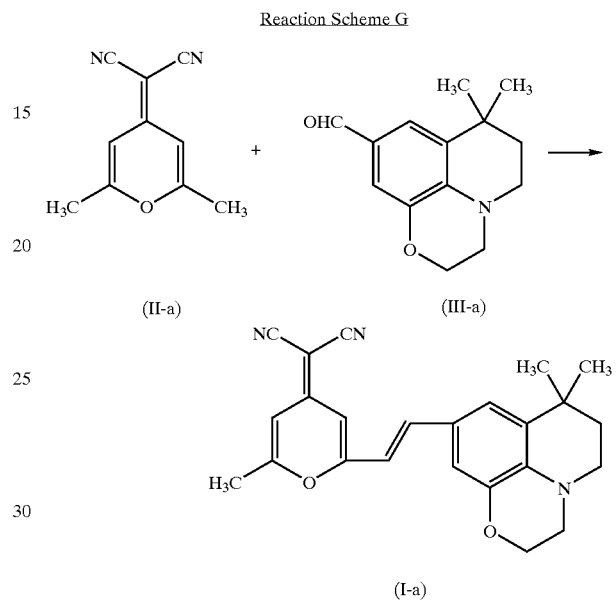

(I-a)

0.517 g (3.0 mmol) of 4-dicyanomethylene-2,6-dimethyl4H-pyran (compound (II-a)) and 0.694 g (3.0 mmol) of compound (III-a) obtained in Preparation Example 1 were added to 15 ml of ethanol, 0.281 g (3.3 mmol) of piperidine was added thereto and the mixture was refluxed for 12 hours. The solvent was removed from the reaction mixture under a reduced pressure, followed by purification by silica gel chromatography, to obtain 0.55 g (yield: 48%) of the title compound as a dark red solid.

Figure 4:
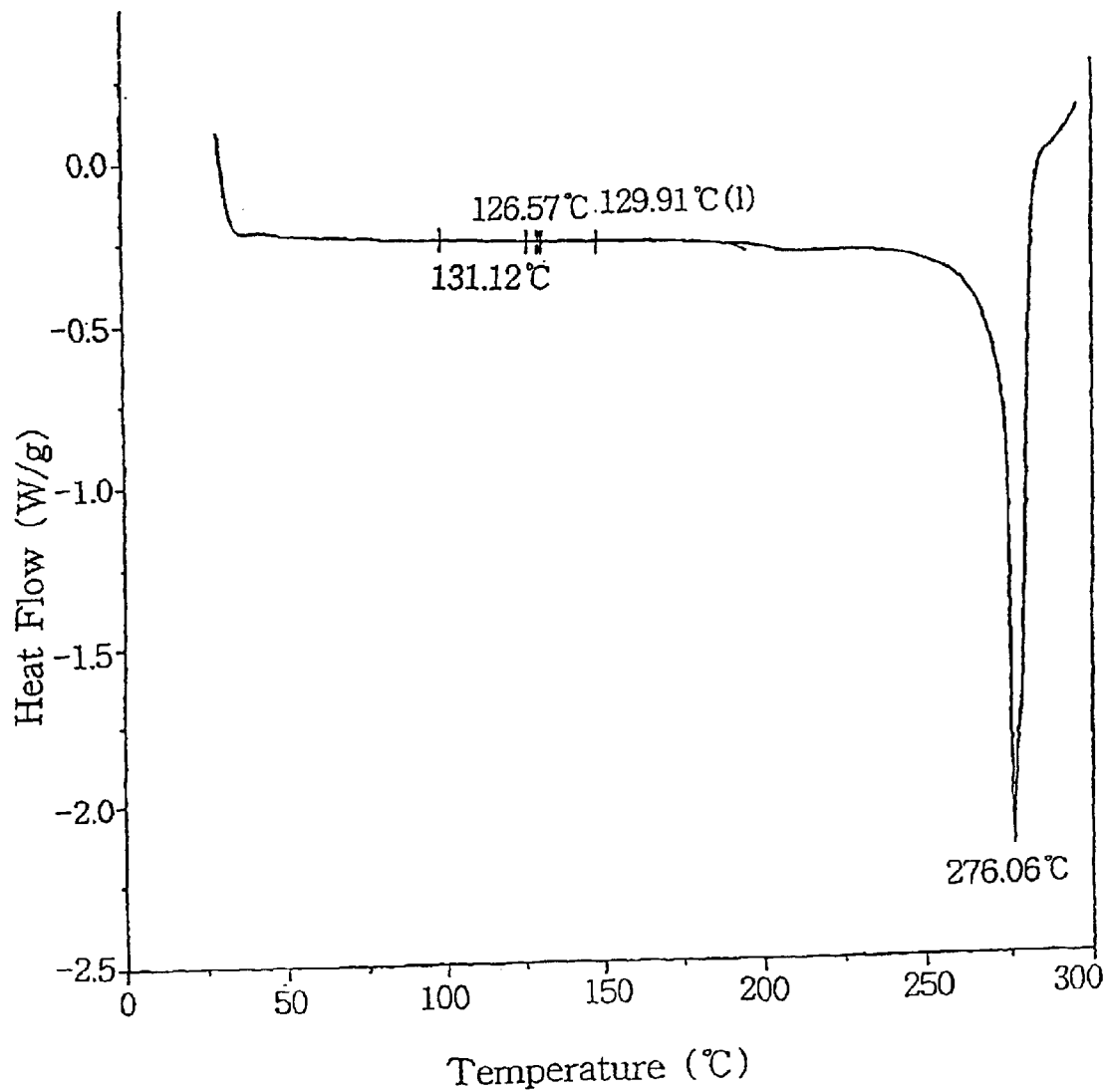
FIG. 4: DSC scan of the compound prepared in Example 1.

The DSC(Differential Scanning Calorimeter) analysis result revealed that the melting point and the glass transition temperature of the title compound are 276° C. and 120° C., respectively. A solution of the title compound in ethylene dichloride exhibited a maximum fluorescence wavelength ranging from 619 nm to 636 nm (from orange to red), depending on its concentration. FIGS. 1 and 4 illustrate NMR and DSC scans of the compound thus obtained, respectively.

EXAMPLES 2 TO 8

Preparation of Compound of Formula (I) of the Present Invention

The procedures of Example 1 were repeated except that 4-dicyanomethylene-2-phenyl-6-methyl-4H-pyran or 4-dicyanomethylene-2-(2,4,6-trimethyl)phenyl-6-methyl-4H-pyran was used instead of 4-dicyanomethylene-2,6-dimethyl-4H-pyran (compound (II-a)), and one compound selected from compounds (III-b), (III-c) and (III-d) obtained in Preparation Examples 2, 3 and 4 was used in place of compound (III-a), to obtain the compounds shown in the Table.

TABLE

| Ex. No. | Structure | Melting point/ glass transition temp. | Fluorescence wavelength (in EDC, nm) | Luminescent color |
|---|---|---|---|---|
| 2 | 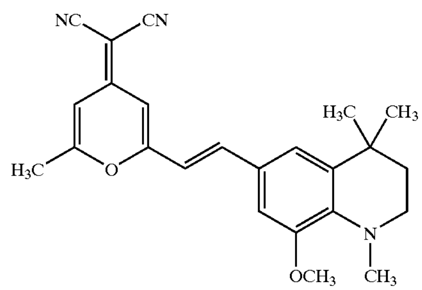 | 255/125 | 649–652 | Orange — Red |
| 3 | 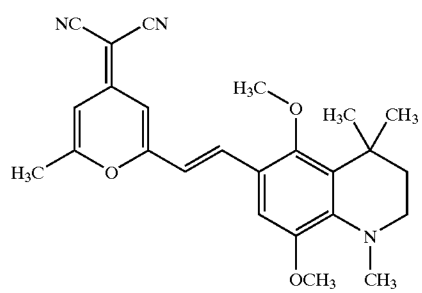 | 227/100 | 651–655 | Orange — Deep red |
| 4 | 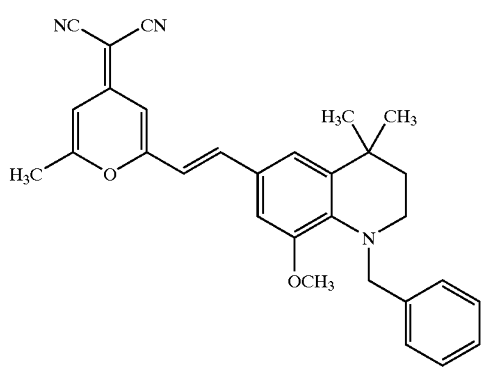 | 260/118 | 630–635 | Orange — Red |
| 5 | 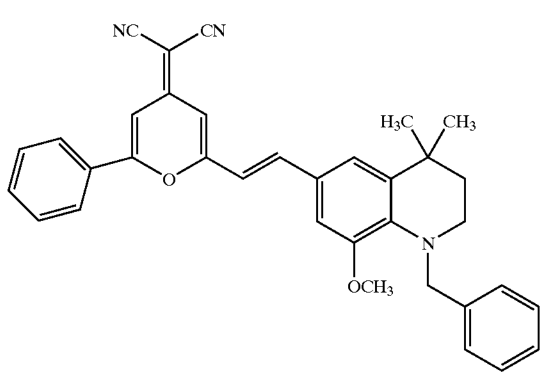 | 300/110 | 661–672 | Red — Deep red |

TABLE-continued

| Ex. No. | Structure | Melting point/ glass transition temp. | Fluorescence wavelength (in EDC, nm) | Luminescent color |
|---|---|---|---|---|
| 6 | 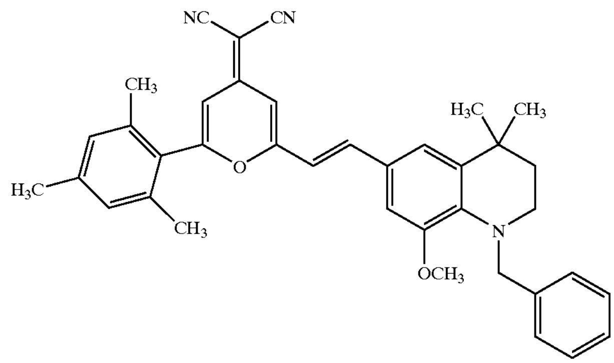 | 275/99 | 647–654 | Red — Deep red |
| 7 | 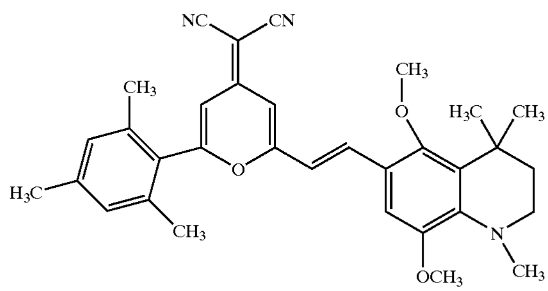 | 251/96 | 663–665 | Red — Deep red |
| 8 | 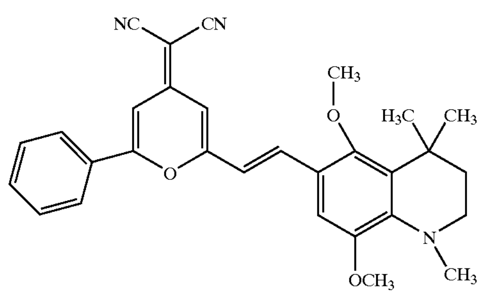 | 178/— | 670–680 | Red — Deep red |

Figure 2:
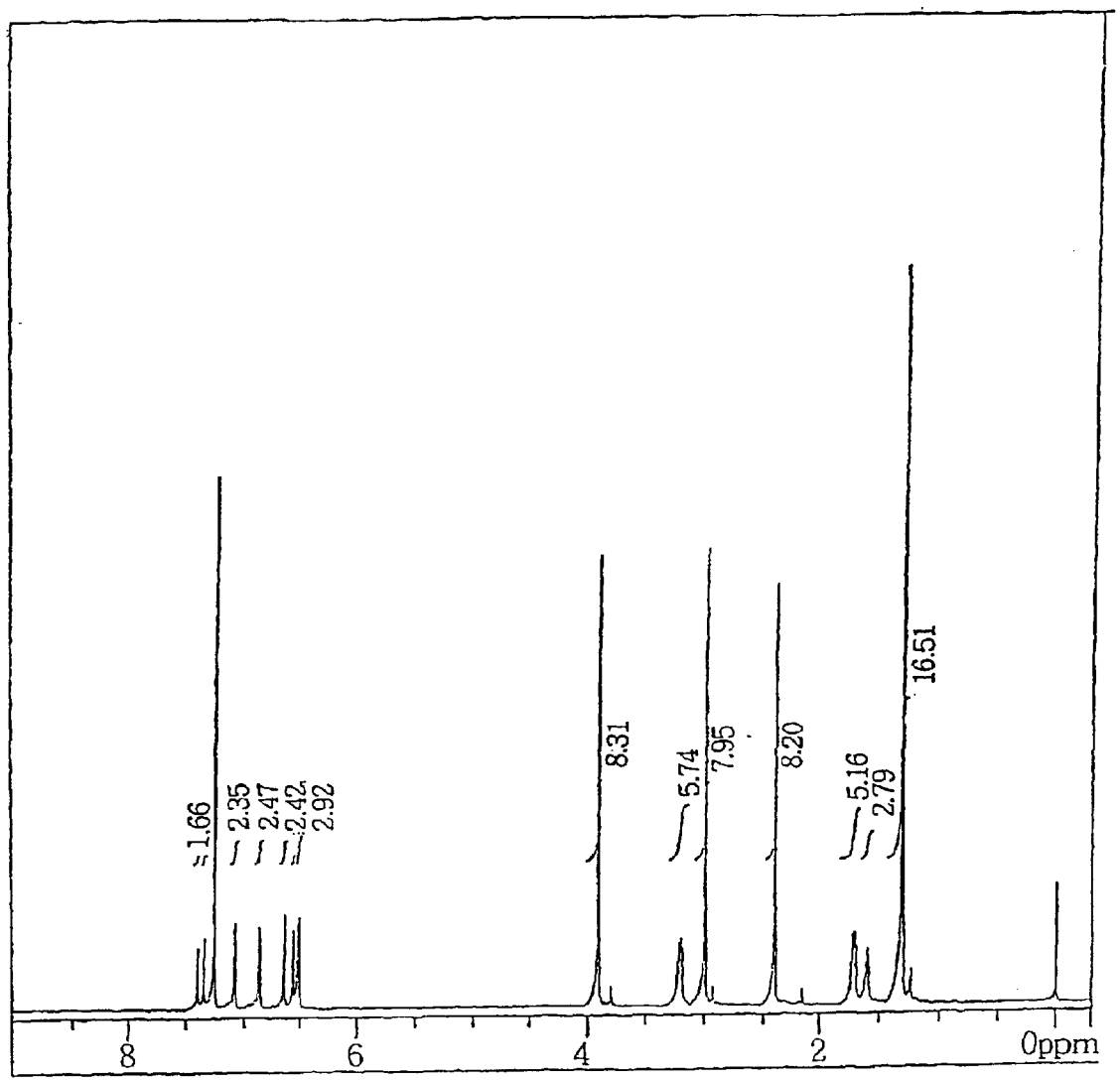
Figure 3:
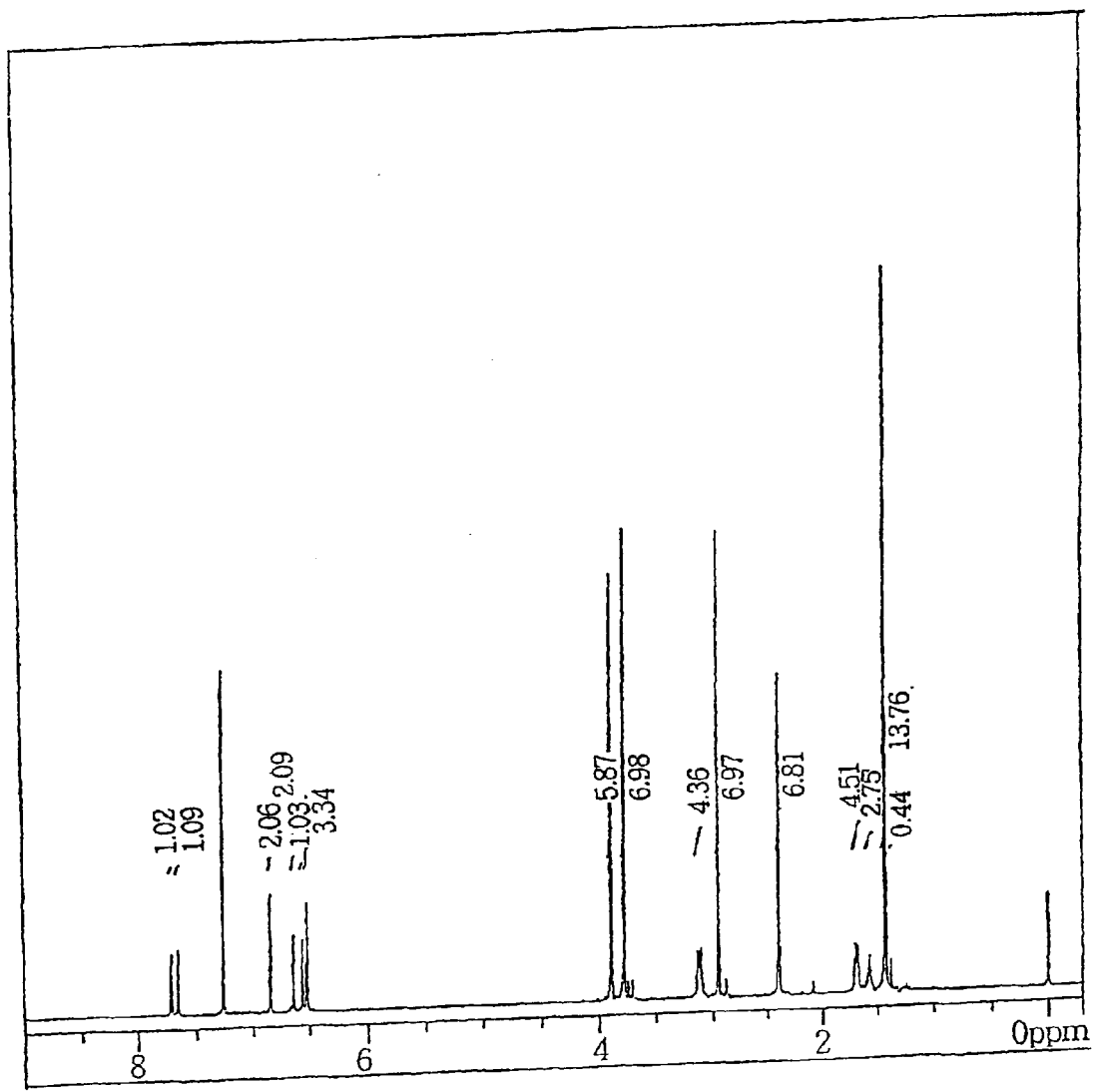
Figure 5:
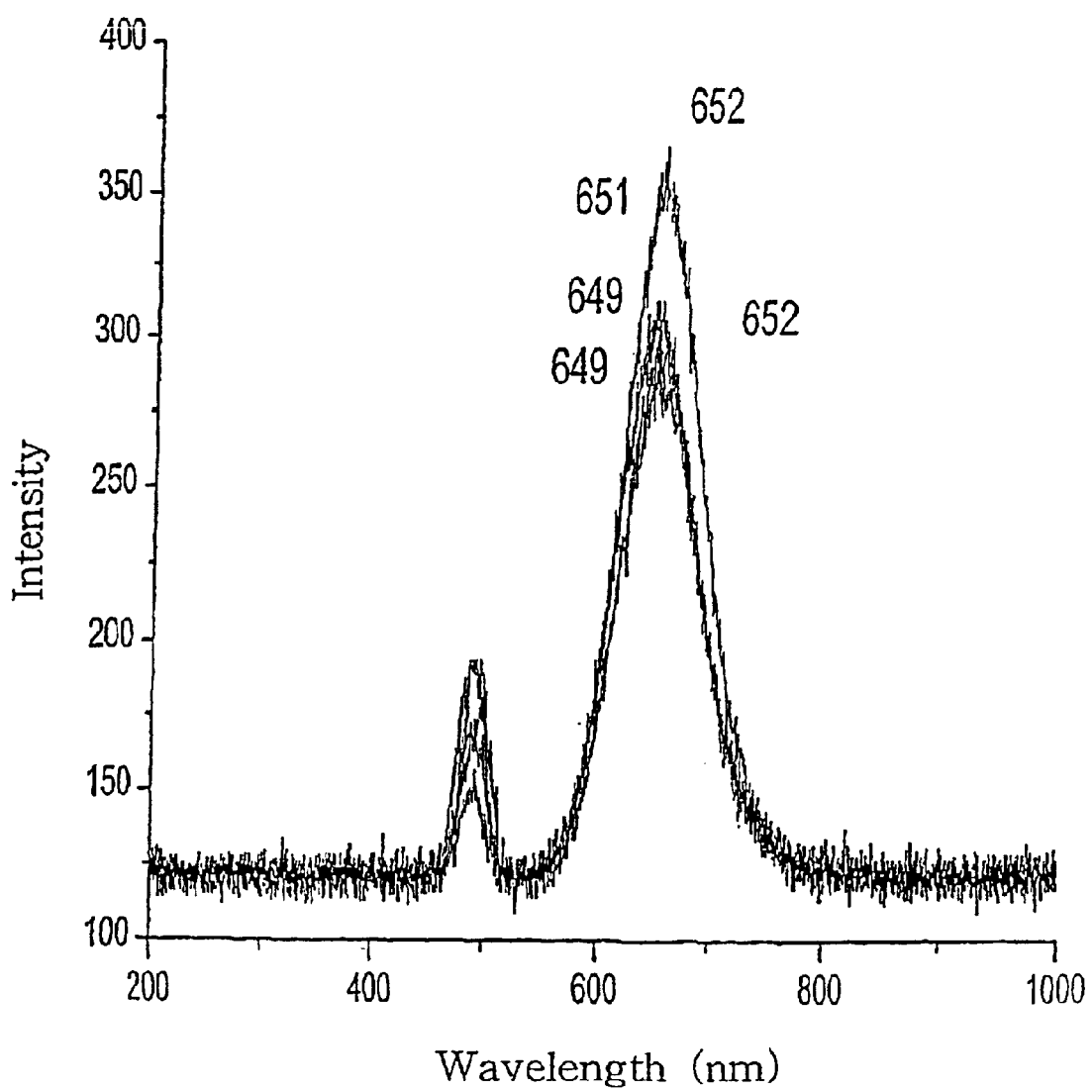
FIG. 5: fluorescence spectrum of the compound prepared in Example 2.

An NMR spectrum of the compound obtained in Example 2 is shown in FIG. 2, and NMR and fluorescence spectra of the compound obtained in Example 3, in FIGS. 3 and 5, respectively.

EXAMPLE 9

Preparation of an Organic Electroluminescent Device

Using the compound obtained in Example 3 as a doping material on a luminescent layer composed of tris(8-hydroquinolinato)aluminum ($Alq_3$) host material, an organic electroluminescent device was prepared in accordance with a conventional method.

First, a 50 nm thick hole transport layer (3) (hole transport material: α-NPD) was formed on an Indium-tin-oxide(ITO) layer (2) formed on a glass substrate (1) at $10^{-6}$ torr. $Alq_3$ doped with the compound obtained in Example 3 to a level of 3% was vapor deposited on the hole transport layer to a thickness of 30 nm at a rate of 0.03 nm/sec to form a luminescent layer (4). Then, an electron transport layer (5) (electron transport material: $Alq_3$) was formed on the luminescent layer to a thickness of 20 nm and, subsequently, aluminum was vapor deposited on the electron transport layer to a thickness of 200 nm at a rate of 1 nm/sec at $10^{-6}$ torr to form a cathode layer (6).

Figure 6:
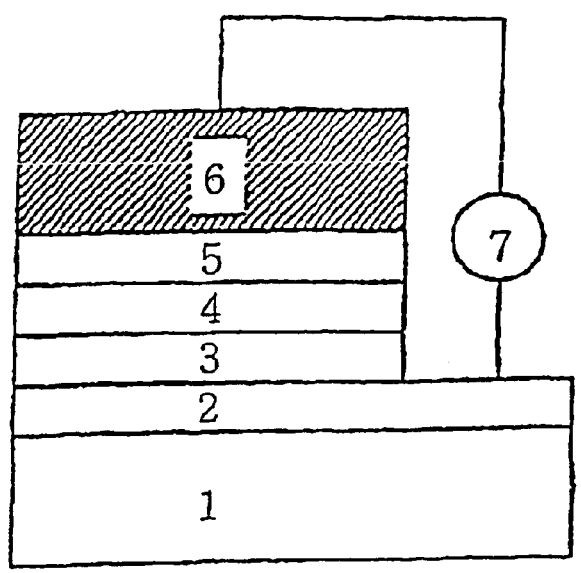
FIG. 6: schematic diagram of an organic electroluminescent device prepared in Example 9.
Figure 7:
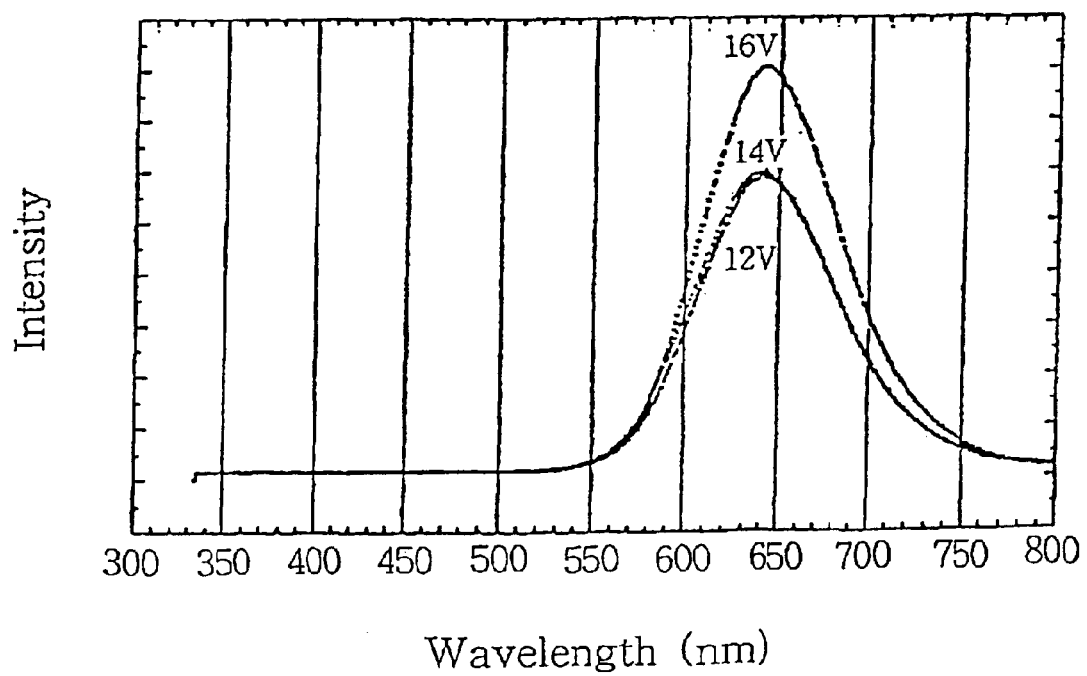
FIGS. 7 to 9: electroluminous spectra, variations of the current density(A/m$^2$) and brightness(cd/m$^2$) as function of applied voltage(V), and change in the luminous efficiency (lm/W) with current density(A/m$^2$), respectively, of the electroluminescent device prepared in Example 9.
Figure 8:
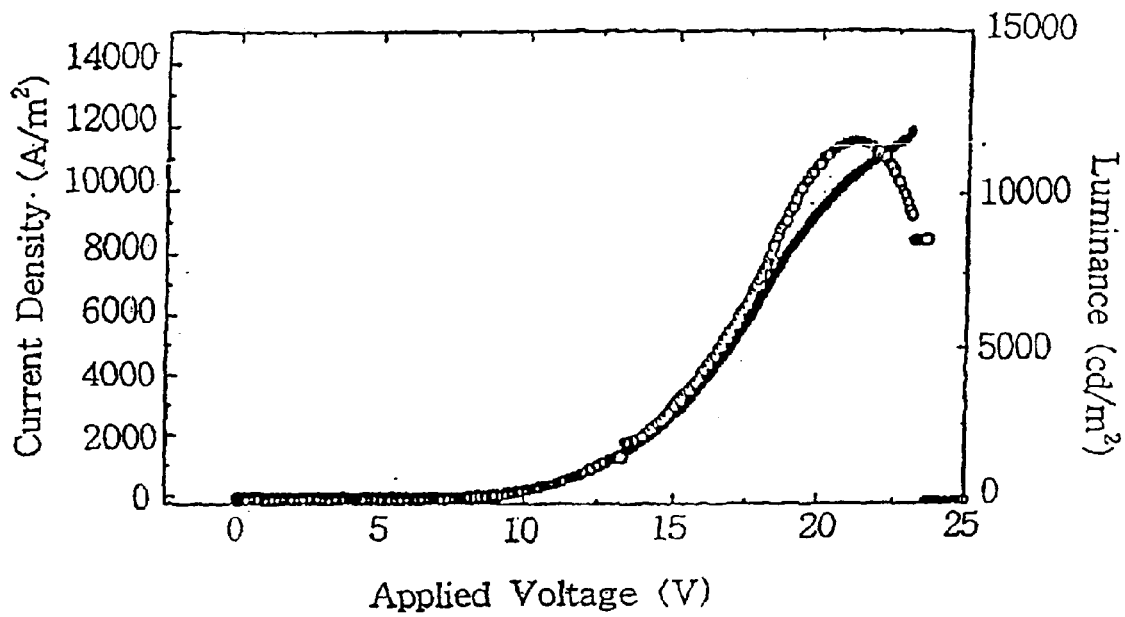
Figure 9:
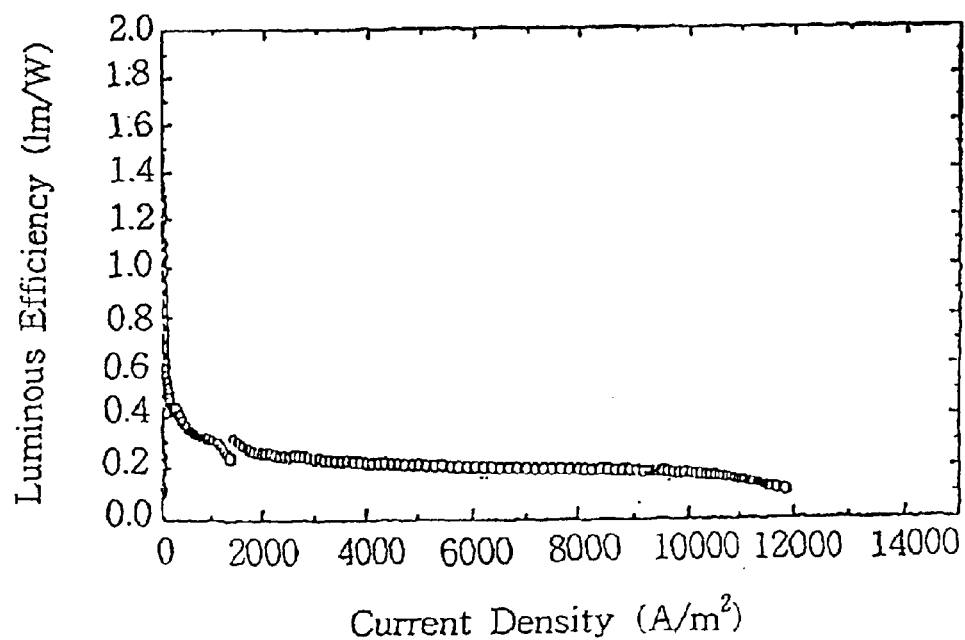

The schematic diagram of the organic electroluminescent device thus obtained is shown in FIG. 6, and the electroluminous spectra, variations of the current density($A/m^2$) and brightness(cd/m$^2$) as function of applied voltage(V), and the change in luminous efficiency(lm/W) with current density (A/m$^2$) of the device are shown in FIGS. 7, 8 and 9, respectively. In FIG. 8, ○ corresponds to the brightness and ●, the current density.

As shown in Figures, the inventive device has stable red luminescence characteristics and can accomplish a high brightness of maximum 12,000 cd/m$^2$ or more.

As can be seen from the above result, the novel fluorescent material of the present invention has improved thermostability and is capable of emitting color in the range of orange to deep red and, therefore, it may be advantageously applied to organic photoconductors, photorefraction thin layer devices, photodiodes and solar cells as well as organic electroluminescent devices.

While the invention has been described with respect to the specific embodiments, it should be recognized that various modifications and changes may be made by those skilled in the art to the invention which also fall within the scope of the invention as defined by the appended claims.

What is claimed is:

1. A red fluorescent compound of formula (I):

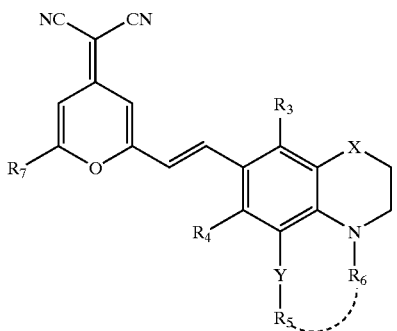

(I)

wherein,

X is CR$_1$R$_2$, NR', oxygen or sulfur;

Y is NH, oxygen or sulfur;

R', R$_1$, R$_2$, R$_3$, R$_4$, R$_5$, R$_6$ and R$_7$ are each independently hydrogen, C$_{1-4}$ alkyl, C$_{1-4}$ alkoxy, aryl, or aryl substituted with C$_{1-4}$ alkyl or C$_{1-4}$ alkoxy, R$_5$ and R$_6$ being optionally fused to form a hetero-ring.

2. The compound of claim 1, wherein X is CR$_1$R$_2$ or oxygen, Y is oxygen or sulfur, and R' and R$_1$ to R$_7$ are each independently hydrogen, methyl, isopropyl, t-butyl, methoxy, phenyl, phenyl substituted with methyl, or benzyl.

3. The compound of claim 1, which is selected from the group consisting of:

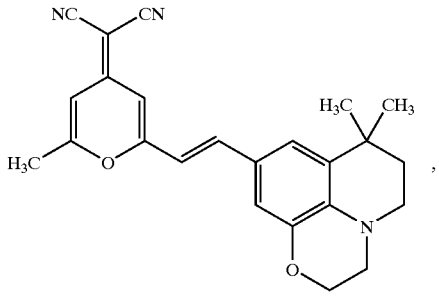

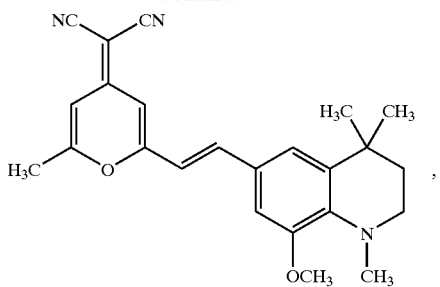

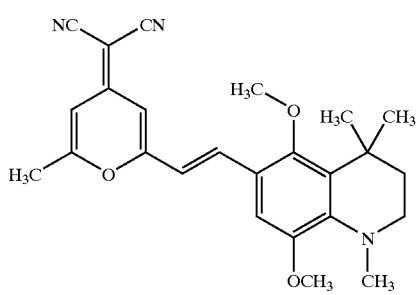

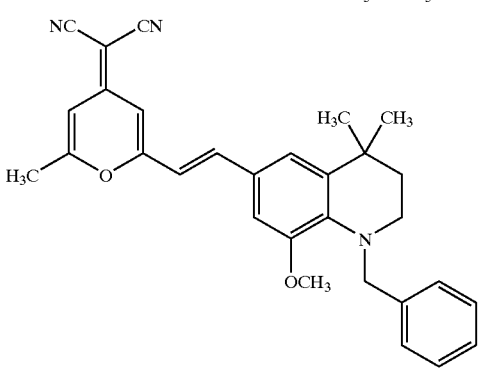

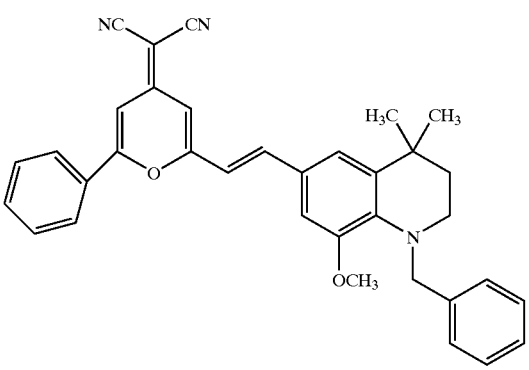

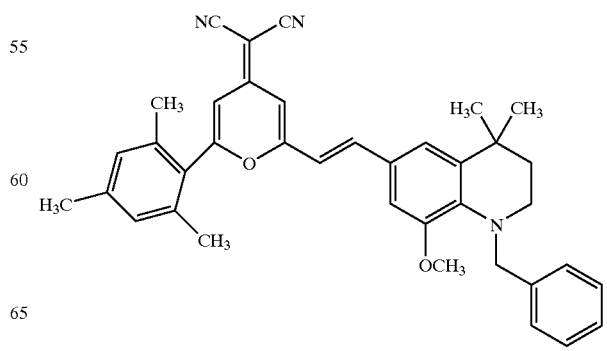

-continued

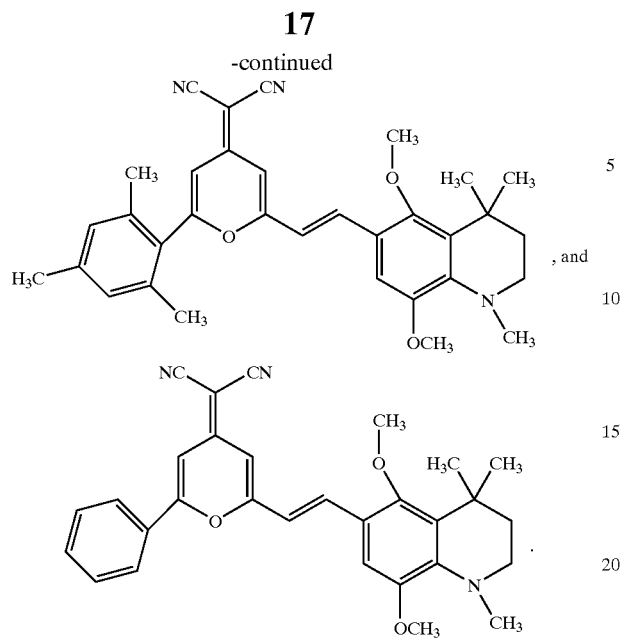

, and

4. A process of preparing the compound of claim 1, which comprises reacting a pyrane derivative of formula (II) with an aldehyde of formula (III) in an alcohol solvent in the presence of a base:

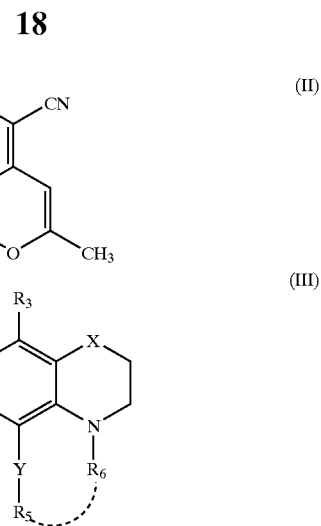

wherein, X, Y, R', and $R_1$ to $R_7$ have the same meanings as defined in claim 1.

5. An organic electroluminescent device comprising an organic luminescent layer containing the compound of claim 1.

6. The organic electroluminescent device of claim 5, wherein the fluorescent compound is used as a doping material for red or orange luminescence.

* * * * *